United States Patent [19]

Kuzmak

[11] Patent Number: 5,226,429
[45] Date of Patent: Jul. 13, 1993

[54] LAPAROSCOPIC GASTRIC BAND AND METHOD

[75] Inventor: Lubomyr I. Kuzmak, Livingston, N.J.

[73] Assignee: Inamed Development Co., Carpinteria, Calif.

[21] Appl. No.: 719,123

[22] Filed: Jun. 20, 1991

[51] Int. Cl.⁵ .................. A61B 19/00; A61B 5/103
[52] U.S. Cl. ................................. 128/898; 606/157; 128/780; 604/28
[58] Field of Search ............ 606/151, 157, 195; 604/97, 99, 51, 28; 128/898, 780

[56] References Cited

U.S. PATENT DOCUMENTS

| | | |
|---|---|---|
| 4,592,355 | 6/1986 | Antebi ................................. 606/157 |
| 4,696,288 | 9/1987 | Kuzmak et al. ..................... 128/780 |
| 5,074,868 | 12/1991 | Kuzmak .............................. 606/157 |

Primary Examiner—Stephen C. Pellegrino
Assistant Examiner—Gary Jackson
Attorney, Agent, or Firm—Michael G. Petit

[57] ABSTRACT

A gastric band adapted for laparoscopic placement around the stomach and a method for deploying the band is described. The band is useful for creating a small pouch with a reinforced stoma in the stomach for the treatment of obesity. A first cannula is introduced into the abdominal cavity. Following gas insufflation, a camera for observing the placement of the band is introduced into the abdominal cavity by means of the first cannula. Two additional second and third cannulas are placed within the abdomen. The gastric band, which has a head end, a tail end and a body portion therebetween, is introduced into the abdomen by means of the second cannula. As the band emerges from the second cannula, an endoscopically-guided snare passed through the third cannula grasps one end of the band and pulls it into an encircling position around the stomach. The tail end of the band is adjustably attached to the head end to form a loop around the stomach. The band is tightened until the stoma has the desired size. The band is then secured against slippage. In a preferred embodiment, the body portion of the band has an inflatable balloon on its stomach-contacting surface. Following implantation, the stoma size in the stomach may be adjusted by removal or injection of fluid into the balloon by means of an injection reservoir.

2 Claims, 8 Drawing Sheets

LAPAROSCOPIC GASTRIC BAND AND METHOD

REFERENCE TO COPENDING PATENT APPLICATION

Reference to copending U.S. patent application Ser. No. 07,562,391 filed Aug. 3, 1990, now U.S. Pat. No. 5,074,868, made by the same inventor is referenced herein.

BACKGROUND

1. Field of the Invention

This invention relates in general to a laparoscopic surgical procedure for the treatment of morbid obesity and, more particularly, to a novel gastric band and a method for the laparoscopic placement of the band.

2. Prior Art

Methods that have been used in the prior art to treat morbid obesity include gastric bypass and small bowel bypass surgery. Stapling of portions of the stomach has also been used to treat morbid obesity. This includes both vertical and horizontal stapling and other variations which will reduce the size of the stomach and make a small stoma opening. Many problems have been associated with the use of staples. First, staples are undependable. Second, they may cause perforations in the stomach wall. And third, the pouch or the stoma formed by the staples may become enlarged over time making the procedure useless.

A more promising method employs the placement of a band around a portion of the stomach by open surgery thereby compressing the stomach and creating a stoma that is less than the normal interior diameter of the stomach. The constricted stoma restricts food intake into the lower digestive portion of the stomach. Such a band has been described by Kuzmak et al in U.S. Pat. No. 4,592,339. In its simplest form the gastric band comprises a substantially nonextensible belt-like strap which constrictively encircles the outside of the stomach thereby producing a new stoma and preventing it from expanding.

Although the banding procedure has great promise due to its simplicity and the fact that it retains the desired diameter of the stoma once established, it is necessary to establish a proper stoma size. To overcome this problem, Kuzmak in U.S. Pat. No. 4,696,288, describes a calibrating apparatus and method for using with a gastric banding device. The calibrating apparatus facilitates controlling the size of the stoma with the gastric band.

In the above-cited '339 patent Kuzmak et al also describe a band which includes a balloon-like section that is expandable and deflatable by injection or removal of fluid from the balloon through a remote injection site. The balloon-like expandable section is used to adjust the size of the stoma both intraoperatively and postoperatively. Such a device is referred to as a stoma-adjustable gastric band.

To facilitate the removal of a gastric band without the need for major surgery, Kuzmak, in U.S. patent application Ser. No. 07/562,391, filed Aug. 3, 1990, describes a gastric banding device with means thereon for removal of the band without the necessity for major surgery. The gastric band of the '391 patent application (referred to herein as a "reversible gastric band") has a actuator cord, one end of which (the distal end) is implanted in the right anterior rectus sheath of a patient, the other end being in contact with a means on the band for severing the loop about the stomach. In practice, the reversible gastric band is operatively placed to encircle the stomach by means of open major surgery. Once in position about the stomach, the reversible gastric band is held securely with sutures on the outside of the stomach thereby prohibiting the encircled stoma from expanding. If, following implantation, it becomes necessary or desirable to remove the reversible gastric band, a remotely actuated releasing portion on the band is activated by means of the actuator cord thereby permitting the removal of the gastric band without major surgery. In addition to having a remotely actuated releasing portion, most preferred embodiments of the reversible gastric band include a flexible substantially non-extensible band portion having an expandable, balloon-like section that is in fluid communication with a remote injection site. The expandable section is used to adjust the size of the stoma either during or following implantation.

Although the ability to adjust and/or remove the gastric band from the abdomen of a patient without the need for open major surgery is a great improvement in the art, it would be especially desirable (particularly from the patient's point of view) to provide a gastric band which may be both deployed in an encircling position around the stomach of a patient and removed from the abdomen without the need for open surgery.

Laparoscopy is a frequently used, relatively conservative modality for gaining entry to the abdominal cavity for diagnostic or therapeutic purposes. The recent popularity of laparoscopic cholecystectomy ("Laparoscopic Cholecystectomy: An Initial Report" by B. A. Salky, et al Gastrointestinal Endoscopy, Volume 37 No. 1, pp 1-4 (1991)) has further stimulated interest in laparoscopic surgical techniques and the development of surgical laparoscopic instruments.

The major patient benefits of laparoscopic surgical procedures are less trauma, less risk of pneumonia due to immediate ambulation, shorter hospital stay, and faster recovery time. Laparoscopic surgery eliminates the large abdominal incision and significantly decreases post-operative pain. Patients may be discharged the next day or even the same day and can resume normal activities within a week.

A laparoscopic surgical procedure is different than an open procedure because all manipulations are done using instruments through small diameter cannulas inserted into the peritoneal cavity through the abdominal wall. The procedure is technically more demanding than through an open incision, and, at least initially, may take longer as the team is learning the new technique. Not only are novel instruments needed for working through a cannula but the work itself must be observed on a 2-dimensional video display. Thus, the surgeon is unable to use the sense of touch and must perform surgery using novel instruments without the benefit of depth perception.

A major problem associated with inserting a prior art band laparoscopically around the stomach is the fact that the stomach is adhered to tissues posterior to the stomach and dissection of these posterior tissues laparoscopically appeared formidable. Potential problems include poor visibility, possible perforation of the stomach, damage to the surrounding organs, hemorrhage and vagus nerve damage. Placing and securely attaching prior art gastric bands laparoscopically would be very difficult or impossible These challenges have encouraged the present inventor to develop both a gastric band suitable for laparoscopic placement and a procedure for its deployment around the stomach. A stoma-adjustable gastric band adapted for laparoscopic placement about the stomach will be referred to herein as a "SLAP gastric band" or, alternatively, as a "SLAP band." Such a SLAP gastric band must be capable of being introduced into the abdominal cavity by means of a trocar cannula portal and deployed in an encircling position around the stomach by laparoscopic techniques.

SUMMARY OF THE INVENTION

It is an object of this invention to provide a gastric band adapted to be placed laparoscopically in an encircling position around the stomach.

It is yet another object of this invention to provide a gastric band adapted for laparoscopic placement in an encircling position around the stomach thereby constricting the stomach producing a stoma within the band-encircling portion of the stomach which may be adjusted by the percutaneous injection of a fluid into an injection reservoir which is in fluid communication with the gastric band.

It is yet another object of this invention to provide a laparoscopic method for placing a gastric band around the stomach for adjustment of the stoma eliminating the need for open surgery.

It is still another object of this invention to provide a gastric band which may be placed laparoscopically in an encircling position around the stomach and removed from its encircling position and from within the abdomen without the need for open surgery.

These and other objects of the invention will become apparent as we turn now to the drawings.

DESCRIPTION OF THE PREFERRED EMBODIMENTS

The instruments needed for the laparoscopic placement of the SLAP band are as follows: routine laparoscopic surgical set, a flexible endoscope (length 30-40 cm), modified forceps (length 40-50 cm—the tip of the forceps must hold end of the band), a SLAP banding instrument and SLAP band holder. In addition to the aforesaid instruments, a banding set is required which includes a SLAP band and a Gastrostenometer TM electronic sensor and calibration tube. The SLAP band is particularly adapted with a special head end which makes it easier to push the band through the cannula and easier to position, cinch tight and secure about the stomach.

Prior Art Gastric Band

Figure 2A:
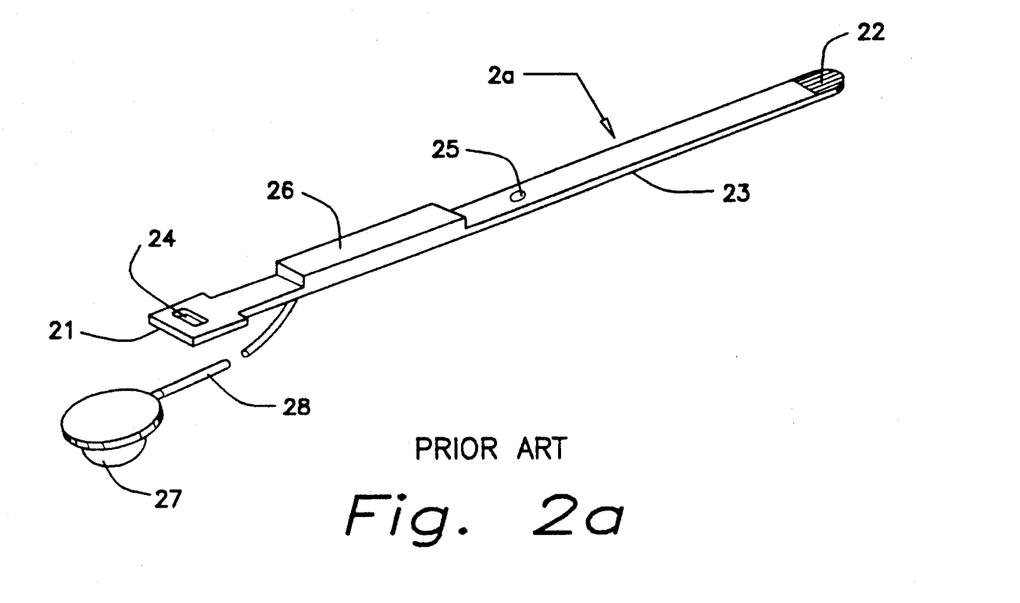
FIG. 2a is a perspective view of a prior art stoma adjustable gastric band.
Figure 2B:
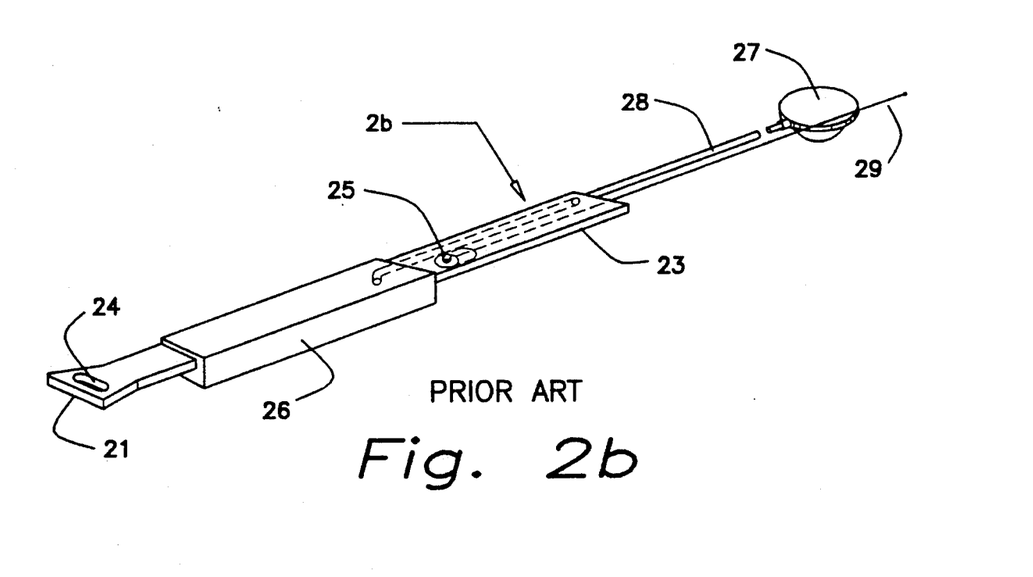
FIG. 2b shows a perspective view of a prior art reversible stoma-adjustable gastric band.

Prior art gastric bands are shown in FIGS. 2a and 2b. A stoma adjustable gastric band, generally indicated at 2a, has a buckle end 21, a tail end 22 and a body portion 23 therebetween. The buckle end 21 has a slot 24 therein to receive the tail end 22 of the band. In practice, the gastric band 2a is placed in an encircling position around the stomach to create a pouch adjacent to the esophagus. The tail end 22 is inserted through the slot 24 in the buckle end 21 and a device is placed in the stomach to indicate the size of the stoma. The band is tightened much as one would cinch a belt until the stoma has the desired size The band is then secured about the stomach by appropriate securing means such as placing sutures through overlapping sections of the band's body portion 23 through a suture hole 25. The stoma measuring device may then be removed from the stomach by the anesthesiologist. A balloon 26 affixed to the interior curvature of the body portion of the band is in fluid communication with a remote injection reservoir 27 by means of a fill tube 28. The surgeon implants the injection port 27 at a suitable location within the rectus sheaths. Postoperative adjustment of the stoma is accomplished by addition or removal of fluid from the balloon 26 by means of a syringe needle (not shown) percutaneously introduced into the injection port 27.

Turning now to FIG. 2b, a reversible stoma-adjustable gastric band generally indicated at 2b, is similar to stoma-adjustable gastric band 2a but has an additional feature permitting remote release of the means securing the band in its encircling position around the stomach. The operative procedure for deployment about the stomach is the same as that described for the placement of the stoma-adjustable gastric band. The portion of the buckle end 21 distal to the slot 24 is removed after the band is secured about the stomach. The distal end of a pull cord or actuator wire 29 is implanted within the rectus sheaths usually adjacent to the injection port 27. If it is desired to remove the band, the distal end of the actuator wire 29 is exposed by superficial incision. The actuator wire may then be manipulated to release of the means securing the band in a loop Once the securing means are released, the entire band may be removed from the patient by pulling on the remotely implanted portion of the band assembly.

The Stoma-Adjustable Laparoscopic Gastric band ("SLAP Band")

The above-described prior art gastric bands are unsuitable for laparoscopic placement because (a) they are not designed to fit through standard laparoscopic cannulas; (b) banding instruments currently used to tighten the prior art gastric bands are not adaptable to laparoscopic use; and (c) placing the tail end of the band through the slot in the buckle end is difficult to perform laparoscopically. A new band design which renders the gastric band, both reversible and non-reversible, suitable for laparoscopic placement is desirable.

Figure 3A:
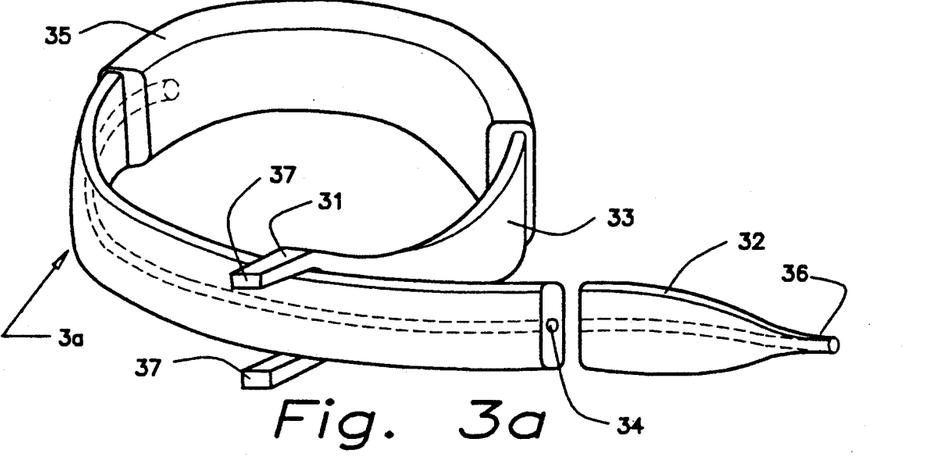
FIG. 3a is a perspective view of a stoma-adjustable gastric band modified according to the present invention for laparoscopic placement.
Figure 3B:
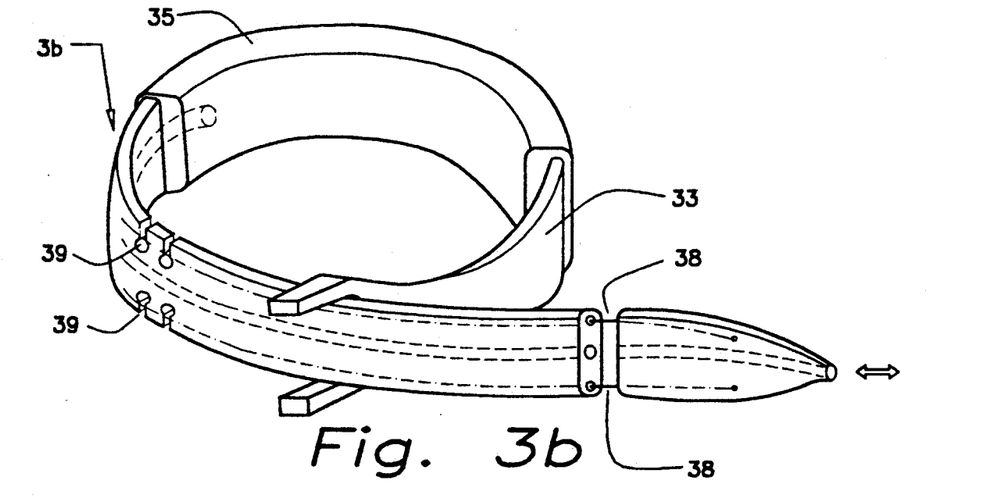
FIG. 3b is a perspective view of a reversible stoma-adjustable gastric band adapted for laparoscopic placement.
Figure 3C:
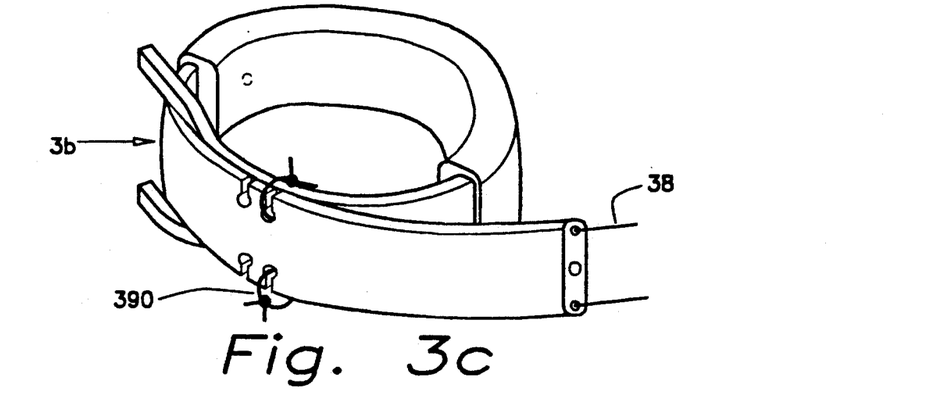
FIG. 3c shows the gastric band of FIG. 3b with sutures securing the band in an encircling position.

A stoma-adjustable embodiment of a gastric band suitable for laparoscopic placement is shown in FIGS. 3a-3c.

The SLAP band, generally indicated at 3a, preferably has a natural flexible curvature as shown and a head end 31, a tail end 32 and a body portion 33 therebetween. The body portion 33 has a lumen 34 therein providing a channel for fluid communication between the tail end 32 and the interior of a longitudinal inflatable balloon 35 affixed to the inner surface of the body portion 33. The tail end 32 of the SLAP band 3a tapers down to form a fill tube 36. The fill tube 36 extends from the tail end 32 of the SLAP band to connect with an injection port (not shown) implanted within the rectus sheaths at a needle-accessible site remote from the SLAP band. The head end 31 is the widest part of the SLAP band and comprises two tabs 37 which are easily compressed to fit through the laparoscopic cannula thereby overcoming the problem presented by the non-compressible oversized buckle of the prior-art bands.

FIGS. 3b and 3c show a reversible embodiment of the SLAP band 3a. The reversible SLAP band, generally indicated at 3b has one or more actuator wires 38 housed within wire guiding lumens 38 which wires pass through slots 39 in the body portion 33 of the SLAP band. After the reversible SLAP band 3b is laparoscopically placed in its encircling position around the stomach and tightened as will be described later, the overlapping body portion of the SLAP band is sutured together. The securing sutures 390 (FIG. 3c) pass through the slots 39 and around the actuator wire(s) 38. Retraction of the actuator wire(s) 38 pull the wire out of the slot thereby releasing the overlapping body portion of the SLAP band bearing the slots. The band may then be removed by pulling it out through a superficial incision by means of the fill tube 36. Tapering the tail end 32 facilitates removal of the reversible SLAP band by dilating the surrounding tissue to accommodate the SLAP band during withdrawal.

Laparoscopic Procedure for Deploying a LAP Gastric Band

In the discussion that follows, reference is made to FIGS. 4-8. For clarity, the trocar cannulas have been omitted from these figures. It should be understood, however, that all intra-abdominal instruments or exogenous assemblies referred to in the figures pass through a laparoscopic cannula.

Figure 1:
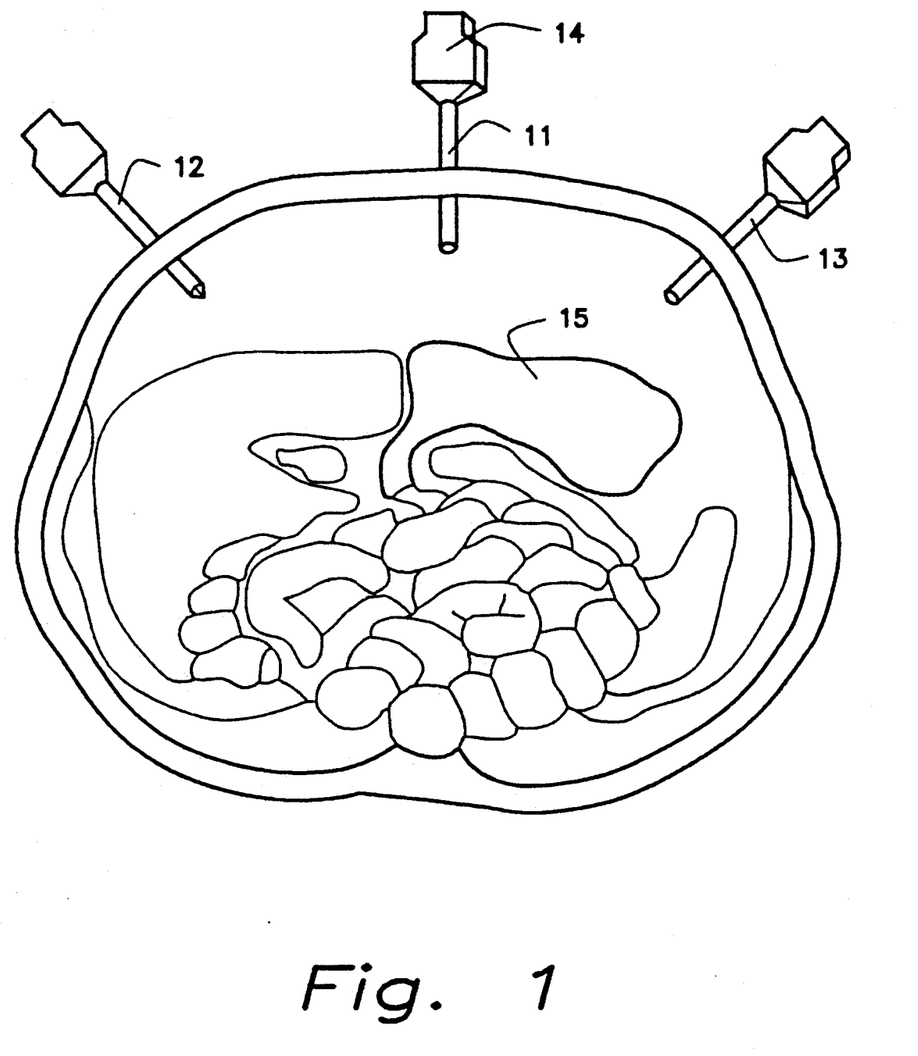
FIG. 1 is a cross-sectional view of the torso of a patient showing the placement of trocars for the introduction of a laparoscopic gastric band.

The surgical technique is as follows:

Step 1. Routine procedures for laparoscopic surgical entrance into the abdominal cavity are followed. Typically, a semicircular incision about 20 mm in length is made at the lower edge of the umbilicus. A trocar 11 (FIG. 1) is inserted through an incision into the peritoneal cavity. The laparoscope 14 is inserted through the sleeve of the trocar 11 and the abdomen insufflated to a pressure of 14-16 mm of mercury. The pressure should never exceed 20 mm of mercury. With abdominal distension, the intraperitoneal viscera are visible. At this time, a video camera (not shown) may be connected to the laparoscope 14. Once the abdomen is properly insufflated, trocars 12 and 13 are inserted under the following guidelines: a) each entrance port is inspected to assure it is a safe area; and b) each insertion is observed through the laparoscope from within to assure no viscera is injured. More additional cannulas may be inserted as the need arises. Once the upper stomach is exposed, adhesions, if present, are transected. The stomach is pulled down (caudal) and the gastrophrenic ligament is opened proximal to the short gastric vessels.

Step 2. Mid-line (2-3") long skin incision in midway between the xyphoid process and the umbilicus. The incision is carried out through the subcutaneous fat to the linea alba. The right rectus sheath is exposed but no space for implantation of the injection port is prepared at this time.

Figure 4:
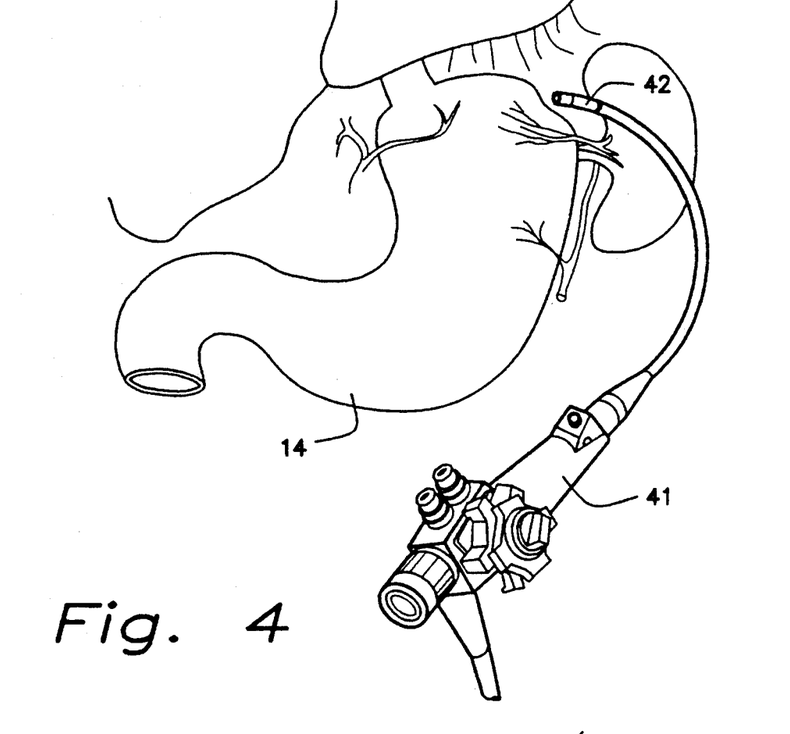
FIG. 4 shows the insertion of a modified flexible endoscope into the upper abdomen.
Figure 5:
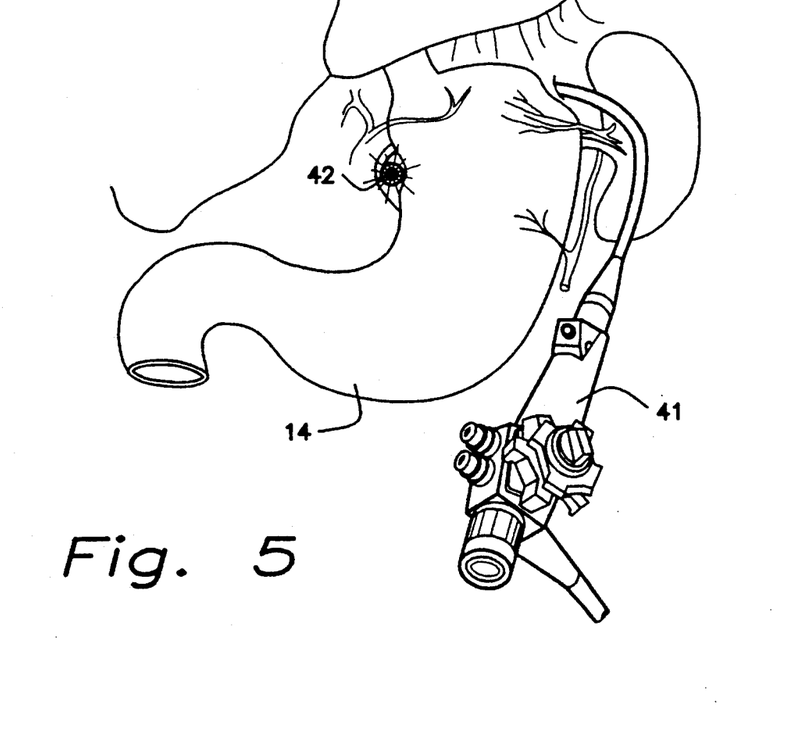
FIG. 5 shows a perspective view of the flexible endoscope with a light on the tip to facilitate dissection along the lesser curvature of the stomach.
Figure 6:
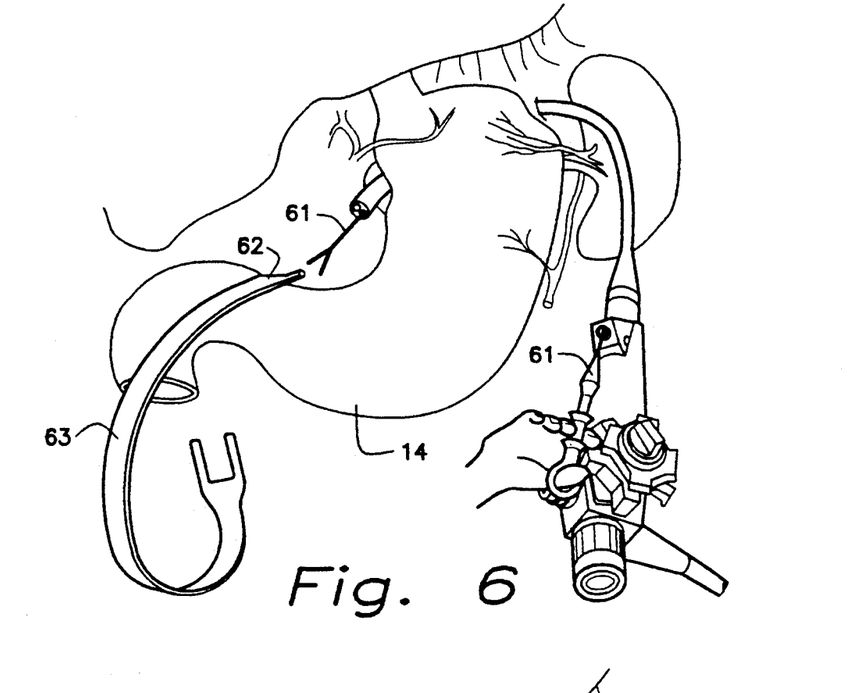
FIG. 6 shows forceps inserted through the lumen of the endoscope prior to grasping the tail end of a SLAP band.

Step 3. As shown in FIG. 4, a modified flexible endoscope 41 is inserted into the abdominal cavity. Using the flexible part 42 of the endoscope 41, blunt dissection is made at the greater curvature. A tunnel is dissected under the stomach toward the lesser curvature as shown by the position of the flexible end 42 of the endoscope 41 in FIG. 5. The optical system of the scope is useful during the dissection. In particular, at the lesser curvature, the light on the scope will make dissection easier and safer (FIG. 5).

Step 4. When the opening next to the lesser curvature is made, forceps 61 (FIG. 6) are inserted through the channel in the scope 41. The tail end of the SLAP gastric band 62 is grasped with the forceps 61 (FIG. 6); and, when withdrawing the endoscope 41, the band is threaded under the stomach. The head and tail ends of the SLAP gastric band are brought together.

Figure 7:
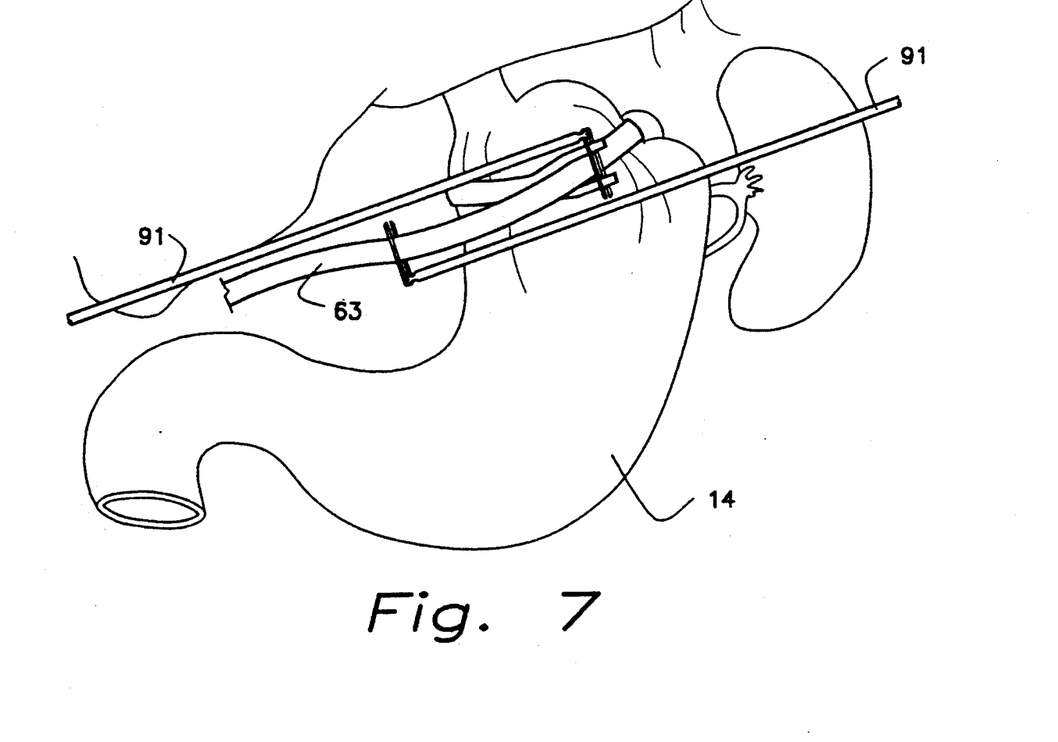
FIG. 7 is a perspective view of the SLAP gastric band being held for adjustment of the stoma size during the calibration procedure.
Figure 9A:
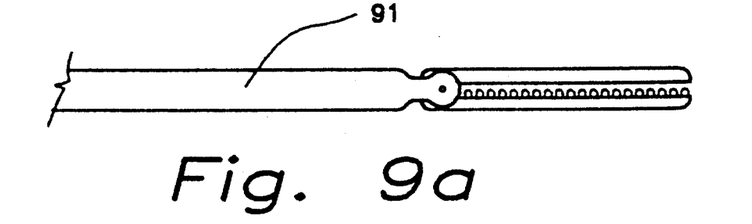
FIG. 9a shows an embodiment of a banding instrument adapted for insertion into the abdominal cavity through a trocar cannula.
Figure 9B:
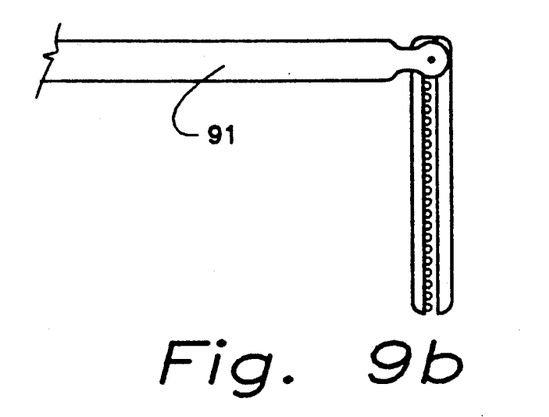
FIG. 9b shows the instrument of FIG. 9a with grasping jaws set at a right angle to the axis of the instrument.
Figure 9C:
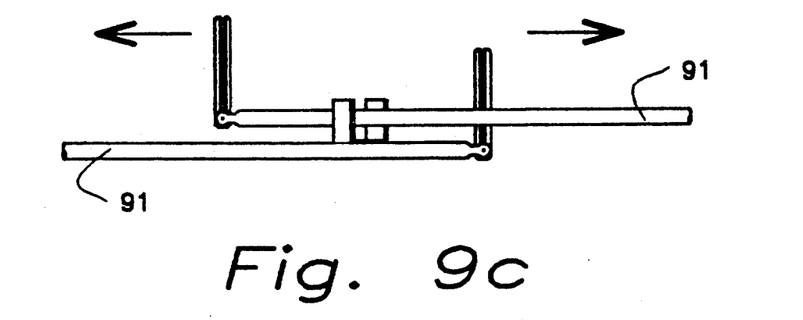
FIG. 9c shows the instrument of FIGS. 9a and 9b modified to interlock with each other.
Figure 9D:
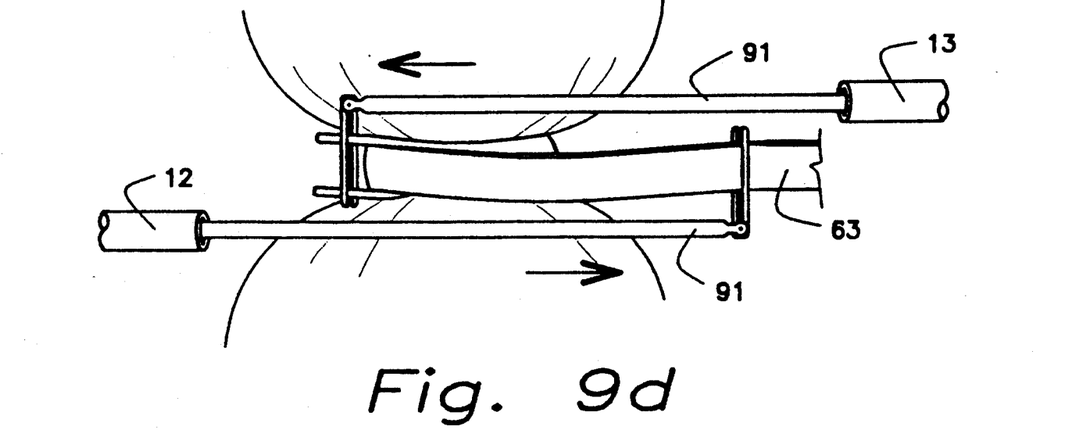
FIG. 9d shows two banding instruments being used with a gastric band to adjust the stoma.

Step 5. A pair of banding instruments 91 (FIG. 9a) are inserted into the abdominal cavity. The head and tail ends of the SLAP gastric band are brought together into adjustable alignment and clamped with the respective jaws of the banding instrument 91 as shown in FIG. 7. The balloon (not shown) on the SLAP band is pre-inflated with saline solution.

Step 6. The calibration tube (not shown) is then inserted into the stomach by the anesthesiologist through the mouth and the SLAP band is tightened by hand until it is firmly in place over the calibration tube in the manner well known in the prior art. The greater curvature is sutured over the SLAP band to the pouch. Using the banding instruments the SLAP band is carefully tightened until the correct stoma diameter is obtained.

Figure 10A:
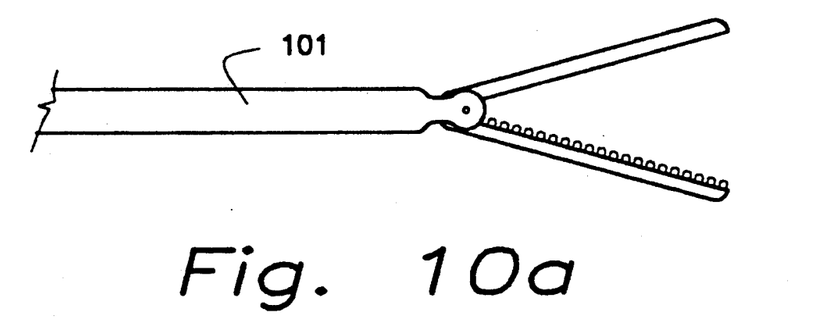
FIG. 10a and 10b shows a gastric band holding instrument in open and closed positions respectively.
Figure 10B:
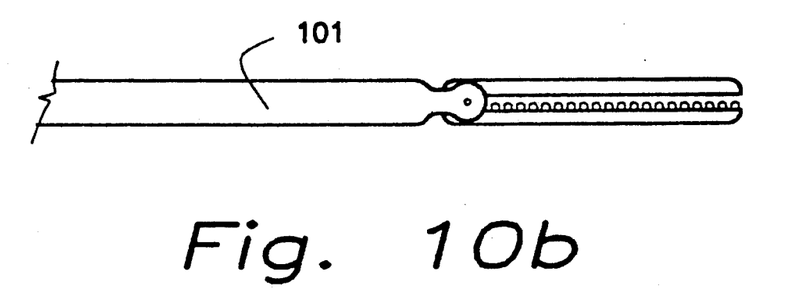

Step 7. The SLAP band holder 101 (FIGS. 10a and 10b) or any other modified attachment device is then applied. The banding instruments and calibration tube are removed.

Step 8. The overlapping ends of the SLAP band are sutured together in the calibrated position (or clipped with clips).

Figure 8:
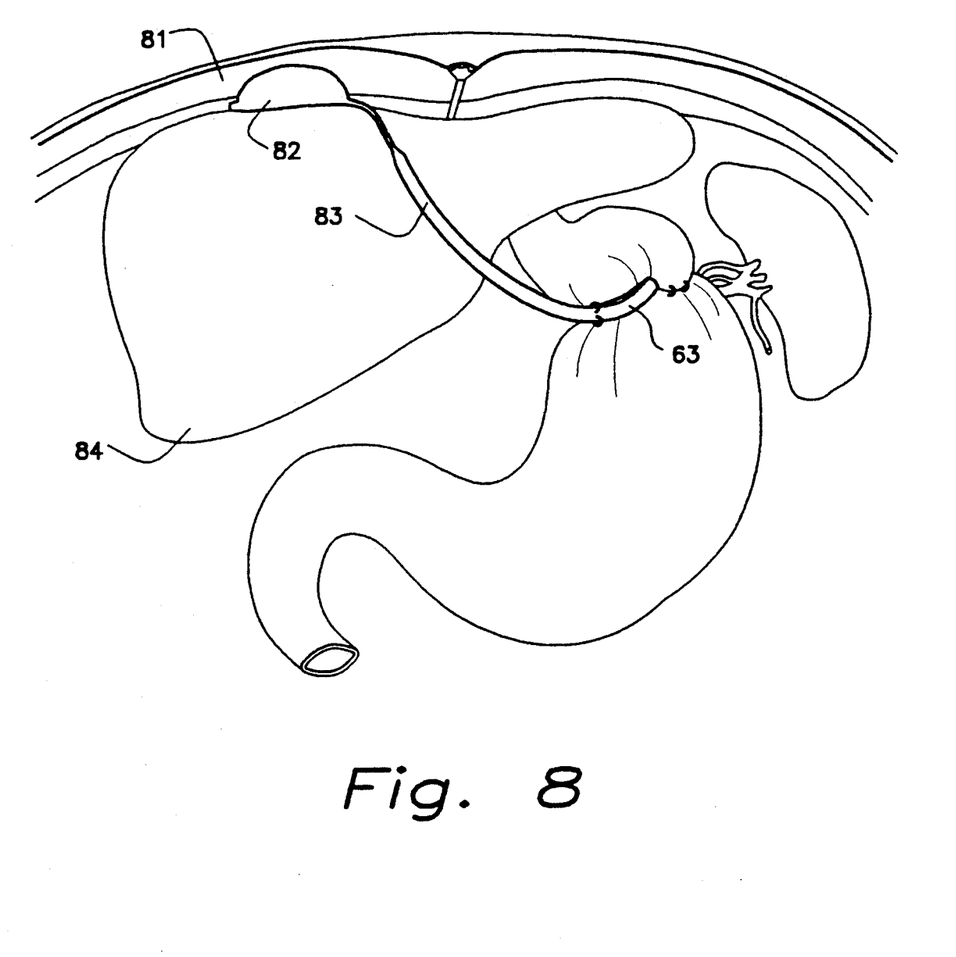
FIG. 8 shows the SLAP gastric band in position around the stomach with an injection port passing underneath the liver and threaded into the space within the rectus sheath for implantation.

Step 9. As shown in FIG. 8, subcutaneous fat overlying the right rectus sheath is dissected for access to the rectus sheaths for implantation of the injection port.

Step 10. The fill tube 83 is placed under the liver 84 to create the shortest path between the SLAP band 63 and the injection site 82 and threaded into the previously dissected receiving space within the rectus sheath. The fill tube 83 is connected to the injection port 82. The incisions are closed in the usual fashion.

It is clear that the foregoing procedure is not only useful for deploying SLAP bands but for deploying any gastric band into an encircling position around the stomach. The SLAP band may have the reversible feature described earlier or it may have no means for either adjustment or reversibility. In the latter case, the band may be conveniently removed laparoscopically provided, of course, that the band has been modified to pass through a cannula.

What I claim is:

1. A method for laparoscopically placing a gastric band in an encircling position around the stomach thereafter to be adjusted by the injection of a fluid into or removal of fluid from an injection port implanted in the rectus sheath, the method comprising the steps of (1) placing several trocars with cannulas within the abdomen; (2) insufflation of the abdomen to create a pneumoperitoneum; (3) dissecting tissue surrounding the stomach to create a path for a gastric band by means of a flexible endoscope inserted into one of the cannulas; (4) introducing a laparoscopic gastric band into the abdominal cavity; (5) grasping said gastric band with a gastric band grasping tool placed through a cannula; and (6) pulling said gastric band to encircling position around the stomach; (7) securing said band about the stomach; (8) threading said fill tube to a point in the rectus sheath; and (9) attaching said fill tube to an injection port.

2. A method for laparoscopically placing a gastric band in an encircling position around the stomach, the method comprising the steps of (1) placing at least one laparoscopic cannula within the abdomen; (2insufflation of the abdomen to create a pneumoperitoneum; (3) placement of at least two additional laparoscopic cannulas within the abdomen; (4) dissection of tissue surrounding the stomach to create a path for gastric band; (5) introducing a gastric band into the abdominal cavity through one of said cannulas; (6) grasping said gastric band with a grasping tool placed through one of said cannulas and pulling said gastric band into an encircling position around the stomach; and, (7) securing said gastric band in said encircling position around the stomach.

* * * * *